(12) United States Patent
Takahashi et al.

(10) Patent No.: US 9,203,507 B2
(45) Date of Patent: Dec. 1, 2015

(54) INFORMATION-GATHERING DEVICE

(71) Applicant: DAI NIPPON PRINTING CO., LTD., Tokyo (JP)

(72) Inventors: Hiroko Takahashi, Tokyo (JP); Takehiko Bizen, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 0 days.

(21) Appl. No.: 14/375,290

(22) PCT Filed: Jan. 22, 2013

(86) PCT No.: PCT/JP2013/051125
§ 371 (c)(1),
(2) Date: Jul. 29, 2014

(87) PCT Pub. No.: WO2013/114997
PCT Pub. Date: Aug. 8, 2013

(65) Prior Publication Data
US 2015/0011166 A1 Jan. 8, 2015

(30) Foreign Application Priority Data

Jan. 30, 2012 (JP) ................................ 2012-017011

(51) Int. Cl.
*H04B 7/00* (2006.01)
*H04B 7/26* (2006.01)
*G06F 19/00* (2011.01)

(52) U.S. Cl.
CPC .............. *H04B 7/26* (2013.01); *G06F 19/3462* (2013.01)

(58) Field of Classification Search
CPC ........................................................ H04B 7/26

USPC ..................................... 455/41.1, 41.2, 556.1
See application file for complete search history.

(56) References Cited

U.S. PATENT DOCUMENTS 6,574,166 B2 6/2003 Niemiec
8,560,012 B2 * 10/2013 Ohnishi et al. ............. 455/556.1
(Continued)

FOREIGN PATENT DOCUMENTS

JP 2000-222485 A1 8/2000
JP 2002-182690 A1 6/2002
(Continued)

OTHER PUBLICATIONS

International Search Report (Application No. PCT/JP2013/051125) dated Apr. 16, 2013.
(Continued)

*Primary Examiner* — Tuan H Nguyen
(74) *Attorney, Agent, or Firm* — Burr & Brown, PLLC (57) ABSTRACT

[Problem] To provide a user-friendly information-gathering device enabling users to select buttons easily.
[Solution to Problem] An information-gathering device 1 has a plurality of selection buttons 6a to 6e and 7a to 7c, a communication module 10, and a cancel button 4. The communication module 10 has an IC chip 12 and a button cell 14. The IC chip 12 has a storage 21 which stores information for identifying the pressed selection button and information about the time of the press, in chronological order, a controller 22 which performs control to store the information in the storage, and a wireless communication unit 23. When the cancel button is pressed, the controller 22 stores, in the storage, information requesting to cancel press information about the selection button pressed immediately before the cancel button is pressed.

10 Claims, 8 Drawing Sheets

(56) References Cited

U.S. PATENT DOCUMENTS

| 2004/0198438 | A1 | 10/2004 | Song et al. |
| 2007/0275361 | A1 | 11/2007 | Tezuka et al. |
| 2008/0053222 | A1 | 3/2008 | Ehrensvard et al. |

FOREIGN PATENT DOCUMENTS

| JP | 2002-367481 | A1 | 12/2002 |
| JP | 2004-503271 | A  | 2/2004 |
| JP | 2007-095577 | A1 | 4/2007 |
| JP | 2008-516248 | A1 | 5/2008 |
| JP | 2009-140165 | A1 | 6/2009 |
| JP | 2010-079637 | A1 | 4/2010 |
| JP | 2011-081708 | A1 | 4/2011 |
| JP | 2011-203197 | A1 | 10/2011 |
| WO | 2005/091248 | A1 | 9/2005 |

OTHER PUBLICATIONS

International Preliminary Report on Patentability (Application No. PCT/JP2013/051125) mailed Aug. 14. 2014.

Japanese Office Action (With English Translation), Japanese Application No. 2012-017011, dated Aug. 28, 2015 (6 pages).

\* cited by examiner

INFORMATION-GATHERING DEVICE

TECHNICAL FIELD

The present invention relates to a sheet-like information-gathering device capable of wirelessly transmitting press information about a button to a host device through a communication module.

BACKGROUND ART

A sheet-like test device made by forming conductive patterns on a sheet through serigraph, and electrically connecting terminals of the conductive patterns to pads of a communication module through conductive adhesive has been put to practical use (see JP-A 2008-516248 (Kokai)).

The test device disclosed in this publication can be sent to a user as a mail. When the user receives it and removes the cover sheet, the user can find some selection buttons and explanations thereof on the inner page. When the user presses an arbitrary selection button in accordance with the explanations, the information is stored in a communication module embedded in a paper substrate, and the stored information can be read into a host device through close proximity wireless communication.

However, in the test device disclosed in JP-A 2008-516248 (Kokai), the user cannot cancel a selection button pressed by mistake, and information about the selection button pressed by mistake is directly transmitted to the host device.

Further, each selection button is connected to a terminal having a different conductive pattern, which means that the total number of selection buttons is limited by the number of terminals of the conductive patterns. Since the size of the paper substrate is limited, it is not easy to increase the number of terminals of the conductive patterns, which makes it impossible to provide many selection buttons.

As another problem, when many selection buttons are provided on the paper substrate, it is not easy for elderly people or disability people to select an appropriate button and it takes much time to read the explanation generally described in small print.

The present invention has been made considering the above problems, to provide a user-friendly information-gathering device enabling users to select buttons easily.

In order to solve the above problems, one aspect of the present invention provides a sheet-like information-gathering device including:

a plurality of selection buttons to be pressed by a user; and a communication module capable of storing at least identification information about the user and information about a pressed selection button, to wirelessly transmit the stored information to a host device has a cancel button to cancel the information about the selection button pressed by the user, wherein the communication module has an IC chip and a button cell which supplies power-supply voltage to this IC chip, the IC chip having:

a storage which stores information which identifies the pressed selection button and information about the time of the press, in chronological order;

a controller which performs control to store the information in the storage; and a wireless communication unit which performs close proximity wireless communication with the host device, the controller, when the cancel button is pressed, to store, in the storage, information requesting to cancel press information about the selection button pressed immediately before the cancel button is pressed.

Further, another aspect of the present invention provides an information-gathering device including:

a plurality of buttons arranged on a first layer of a sheet substrate, to be arbitrarily selected;

a plurality of switch contacts arranged on a second layer of the sheet substrate, corresponding to the buttons;

a terminal unit having a plurality of terminals arranged on a line on the second layer; and a plurality of conductive patterns connecting the switch contacts to the terminals, in which two or more of the buttons are partially arranged in one direction so that one ends of switch contacts corresponding to the buttons are connected to an identical terminal of the terminal unit through the conductive patterns, and that the other ends thereof are connected to a ground terminal of the terminal unit through the conductive patterns.

The present invention can provide a user-friendly information-gathering device enabling users to select buttons easily.

DESCRIPTION OF EMBODIMENTS

Hereinafter, embodiments of the present invention will be explained in detail.

First Embodiment

Figure 1:
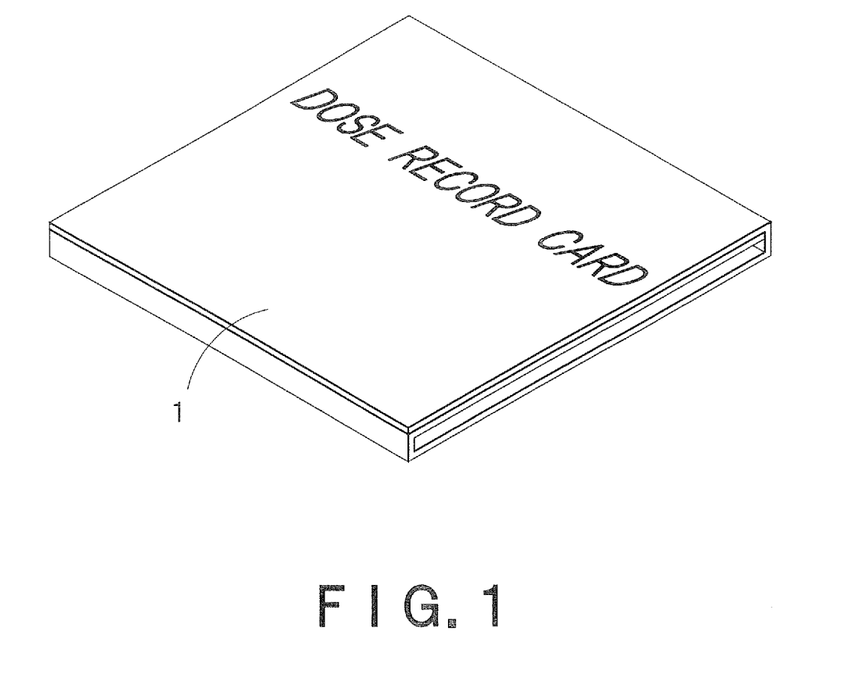
FIG. 1 An external view of an information-gathering device according to a first embodiment of the present invention.

A first embodiment is characterized in recording the date and time when a patient takes medicine and his/her condition after taking the medicine. FIG. 1 is an external view of an information-gathering device according to the first embodiment. The information-gathering device of FIG. 1 is a foldable sheet-like dose record card 1 made of paper or plastic sheet. When unfolding the dose record card 1, an information input face 2 appears as shown in FIG. 2.

After a patient has a medical examination in the hospital and prescription medicine for the patient is dispensed, the dose record card 1 of FIG. 1 is passed to the patient. With this dose record card 1, the patient can record his/her physical condition by pressing selection buttons by him/herself after taking medicine.

Figure 2:
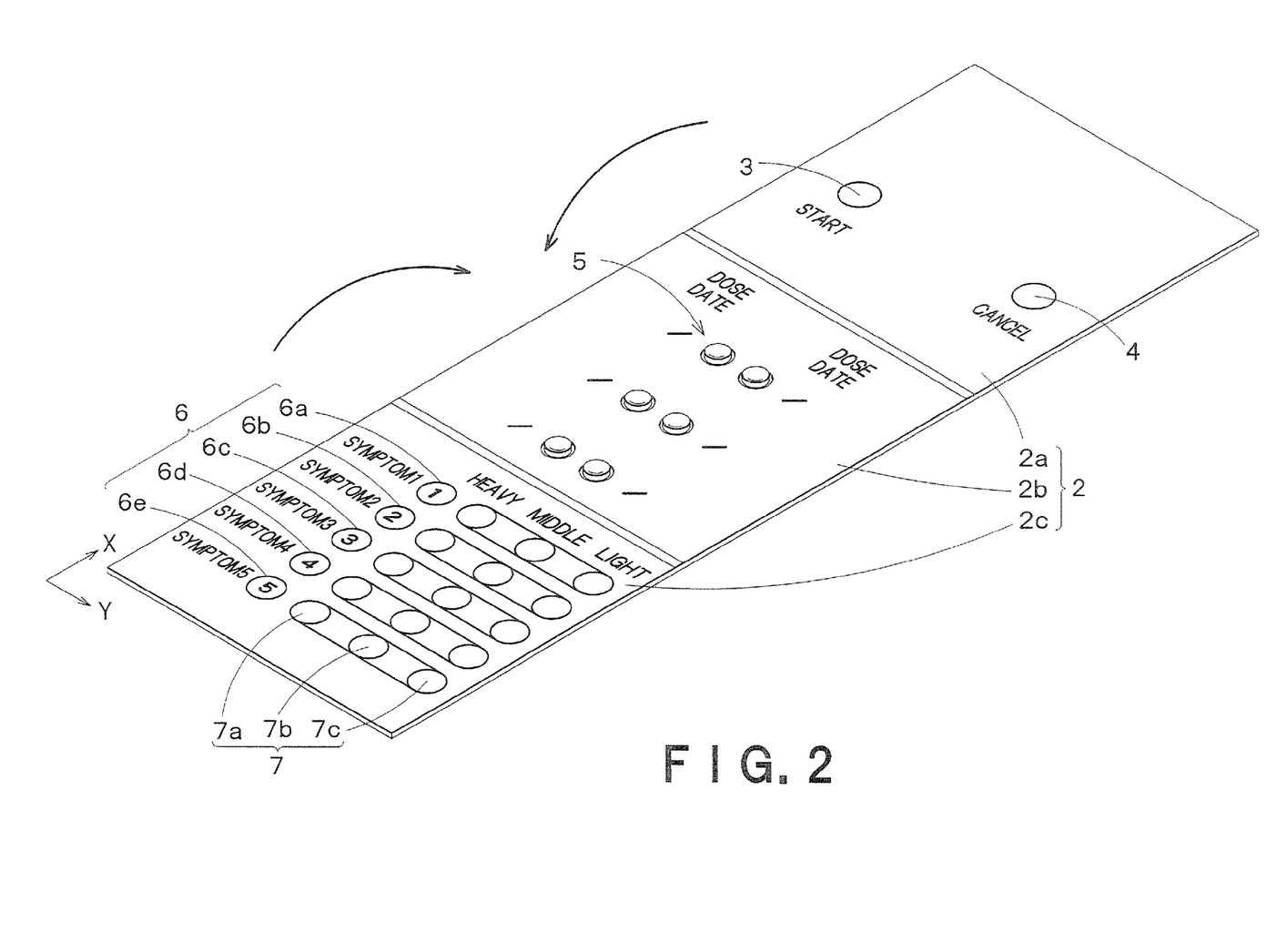
FIG. 2 A development view of the information-gathering device of FIG. 1.

The information input face 2 of the dose record card 1 of FIG. 2 has three faces: a first face 2a having a start button 3 and a cancel button 4; a second face 2b having medicine (pills) 5 to be taken by the patient; and a third face 2c having selection buttons for inputting the symptom level of the patient. The characters "dose record card 1" are described on the back face of the first face 2a, as shown in FIG. 1.

On the third face 2c, a plurality of symptoms are described in relation to the efficacy of the medicine. In the example of FIG. 2, five types of symptoms, which are namely (1) Symptom 1, (2) Symptom 2, (3) Symptom 3, (4) Symptom 4, and (5) Symptom 5, are described, and the patient can select one of three levels (severe, moderate, and mild) concerning each symptom. The patient first selects a specific symptom by pressing any one selection button in a first button line 6 having selection buttons 6a to 6e corresponding to five types of symptoms, and then presses any one selection button in second button lines 7 having selection buttons 7a to 7c corresponding to the levels of each symptom. In this way, the patient can input the level of a specific symptom after taking medicine. The patient is not necessarily required to answer on all of the five types of symptoms, and may answer on only a part of symptoms.

As shown in FIG. 2, the selection buttons 6a to 6e constituting the first button line 6 are arranged in the X-direction, and the selection buttons constituting the second button lines 7 are arranged in the Y-direction to form a plurality of lines nearly in parallel to the first button line 6.

Note that the symptoms and their levels described on the third face 2c are shown merely as an example, and those may be arbitrarily changed depending on the type of medicine.

The patient initially presses the start button 3 when using the dose record card 1. After that, the patient takes medicine by pushing with a finger a case of a pill 5 arranged on the second face 2b to take out the pill 5 from the underside of the second face 2b. Then, the patient presses selection buttons 6 and 7 applicable to the symptom level after taking the medicine.

Information about the start button 3, cancel button 4, cases of the pills 5, and selection buttons 6 and 7 pressed by the patient is automatically stored in a communication module incorporated in the dose record card 1.

Figure 3:
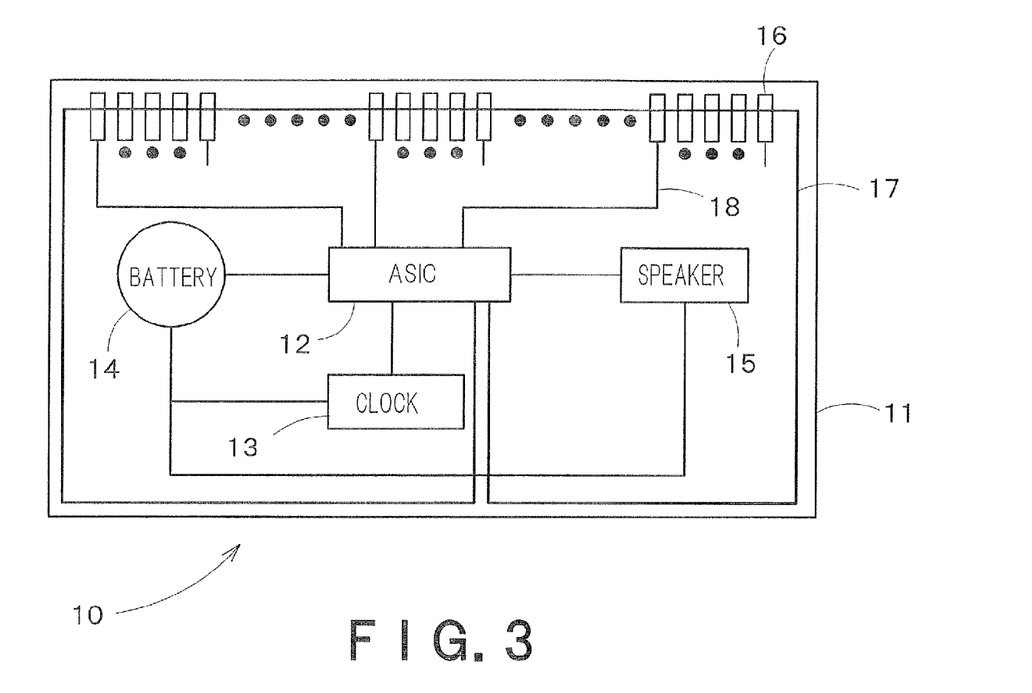
FIG. 3 A block diagram showing a schematic structure of a communication module 10.

FIG. 3 is a block diagram showing a schematic structure of a communication module 10. The communication module 10 of FIG. 3, which is a thin film having a thickness smaller than that of paper, has an ASIC (Application Specific Integrated Circuit) 12 mounted on a film substrate 11, a crystal oscillator 13, a button cell 14, a speaker 15, a plurality of pads 16 formed along the long side of the film substrate 11, an antenna pattern 17 formed along the outer edge of the film substrate 11, and conductive patterns 18 formed on the film substrate 11.

FIG. 3 is a functional block diagram of the internal structure of the communication module 10, and each circuit component and pattern arrangement can be arbitrarily changed in size, shape, and number in the actual configuration.

Figure 4:
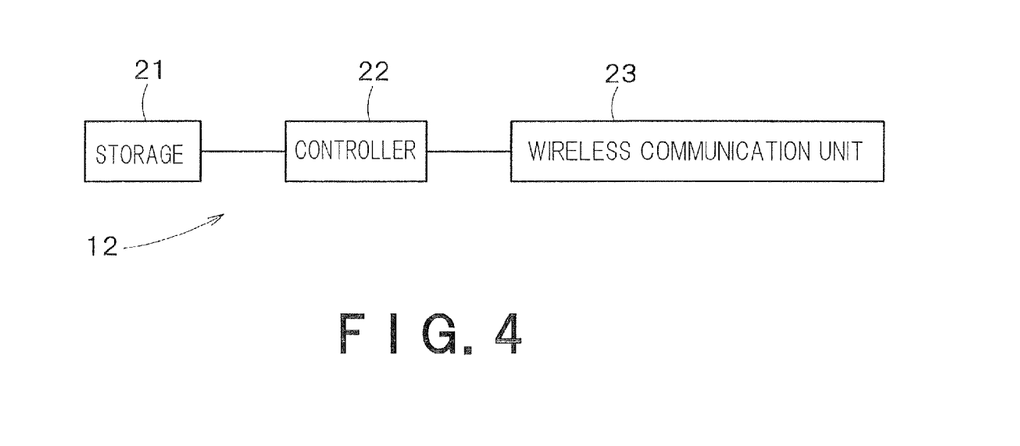
FIG. 4 A block diagram showing an example of the internal structure of an ASIC 12.

FIG. 4 is a block diagram showing an example of the internal structure of the ASIC 12. The ASIC 12 of FIG. 4 has a storage 21 which stores information about the start button 3, cancel button 4, respective cases of the pills 5, and selection buttons, each of buttons being pressed by the patient together with time information in chronological order, a controller 22 which performs control to store the press information in the storage 21, and a wireless communication unit 23 which wirelessly communicates with a host computer (not shown).

The storage 21 stores information for identifying a button pressed by the patient together with information about the time when the button was pressed. The cancel button 4 is provided to cancel the information about the button pressed immediately before the cancel button 4 is pressed. When the storage 21 stores information identifying the press of the cancel button 4 and information about the time when the button was pressed, the host computer cancels the information about the button pressed immediately before the cancel button 4 is pressed.

Such a cancel button 4 makes it possible to cancel the information about the button pressed immediately before the cancel button 4 is pressed. Actually, it is impossible to eliminate or overwrite the information once stored in the storage 21. When incorrect information is stored in the storage 21 by mistake, information showing that the stored information is incorrect is additionally stored by pressing the cancel button 4. This makes it possible for the host computer to simply and correctly judge whether the information read thereby is correct. Further, the patient is freed from a mental burden that no mistake is acceptable, since the patient can redo the button operation as many times as he/she likes.

The wireless communication unit 23 transmits/receives information to/from the host computer through so-called NFC (Near Field Communication, close proximity wireless communication). The system and frequency band used in the wireless communication by the wireless communication unit 23 should not be particularly limited. For example, the wireless communication may be performed in 13.56 MHz band using a wireless method based on ISO 14443.

The NFC, which can transmit and receive power based on its standards, makes it theoretically possible to drive the communication module 10 without a cell. Note that the communication module 10 of the present embodiment has the button cell 14 since it has the speaker 15 consuming relatively large amount of power.

It is inevitable that the button cell 14 is dead after long-term use. Since the dose record card 1 according to the present embodiment is generally made of paper undurable to long-term use, it is based on the assumption that the dose record card 1 itself is exchanged when the battery is dead.

Figure 5:
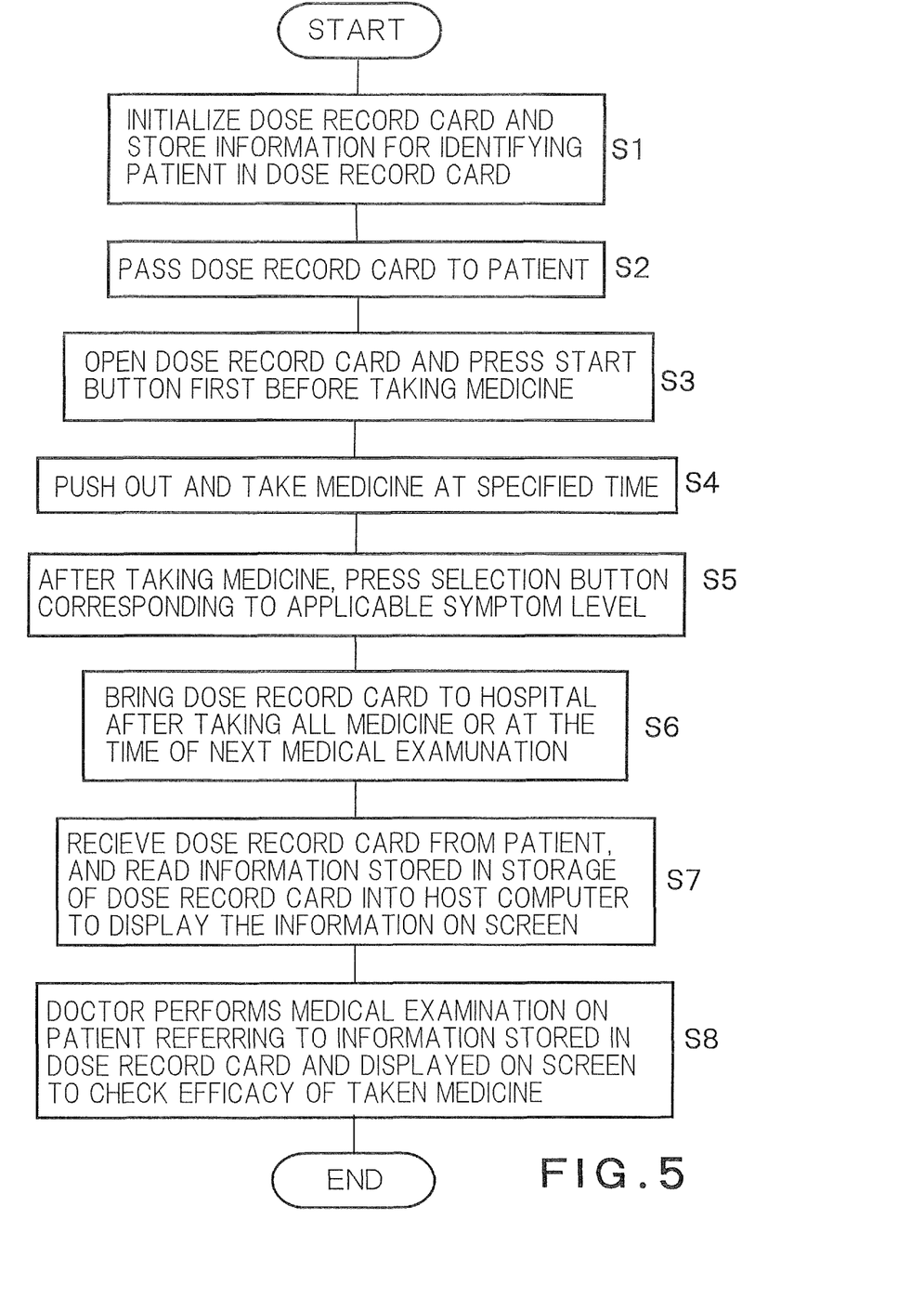
FIG. 5 A flow chart showing an example of a use procedure of a dose record card 1 of FIG. 1.

FIG. 5 is a flow chart showing an example of a use procedure of the dose record card 1 of FIG. 1. First, a doctor or a medical expert in the hospital initializes the dose record card 1 having predetermined prescription medicine embedded therein by passing the dose record card 1 over a reader connected to the host computer, and then information for identifying the patient is stored in the storage 21 in the dose record card 1 (Step S1). Further, date and time when the patient should take the pills are written by hand etc. beside each pill embedded in the second face 2b. This write operation is not essential, and may be handled by the patient as needed.

After that, the dose record card 1 is passed to the patient (Step S2). The patient opens the dose record card 1, and presses the start button 3 first before taking a pill (Step S3). After that, the patient pushes out and takes a pill at a specified time (Step S4).

After taking the pill, the patient presses a selection button corresponding to an applicable symptom level, in accordance with the description on the third face 2c (Step S5).

Press information about the start button 3 and the case of each pill 5 pressed by the patient is automatically stored in the storage 21 of the communication module 10, together with time information. Further, when the start button 3 or selection button is incorrectly pressed, the patient presses the cancel button 4 immediately after the mistake to store, in the storage 21, information showing that the previous press information is incorrect. In this way, incorrect button operation can be practically cancelled.

The patient brings the dose record card 1 to the hospital after taking all medicines or at the time of the next medical examination (Step S6). Then, a doctor or a medical expert in the hospital receives the dose record card 1 from the patient, and passes it over the reader connected to the host computer to read the information stored in the storage 21 of the dose record card 1 into the host computer and to display the information on a screen (Step S7). The doctor performs a medical examination on the patient referring to the information stored in the dose record card 1 and displayed on the screen to check the efficacy of the taken medicine (Step S8).

Since the dose record card 1 stores every symptom felt by the patient after taking the medicine, the doctor can correctly and concretely grasp the symptoms of the patient after taking the prescription medicine in chronological order without relying on the patient's memory, which makes it possible to treat the patient accurately while preventing diagnostic errors.

Next, a concrete structure of the dose record card 1 according to the present embodiment will be explained. The above-mentioned dose record card 1 has a three-layer structure obtained by folding a paper substrate in three in the longitudinal direction so that the information input face 2 shown in FIG. 2 appears on the top face. Further, folding this paper substrate into three in the lateral direction leads to the structure shown in FIG. 1. Hereinafter, conductive patterns formed on a base paper substrate will be explained.

Figure 6:
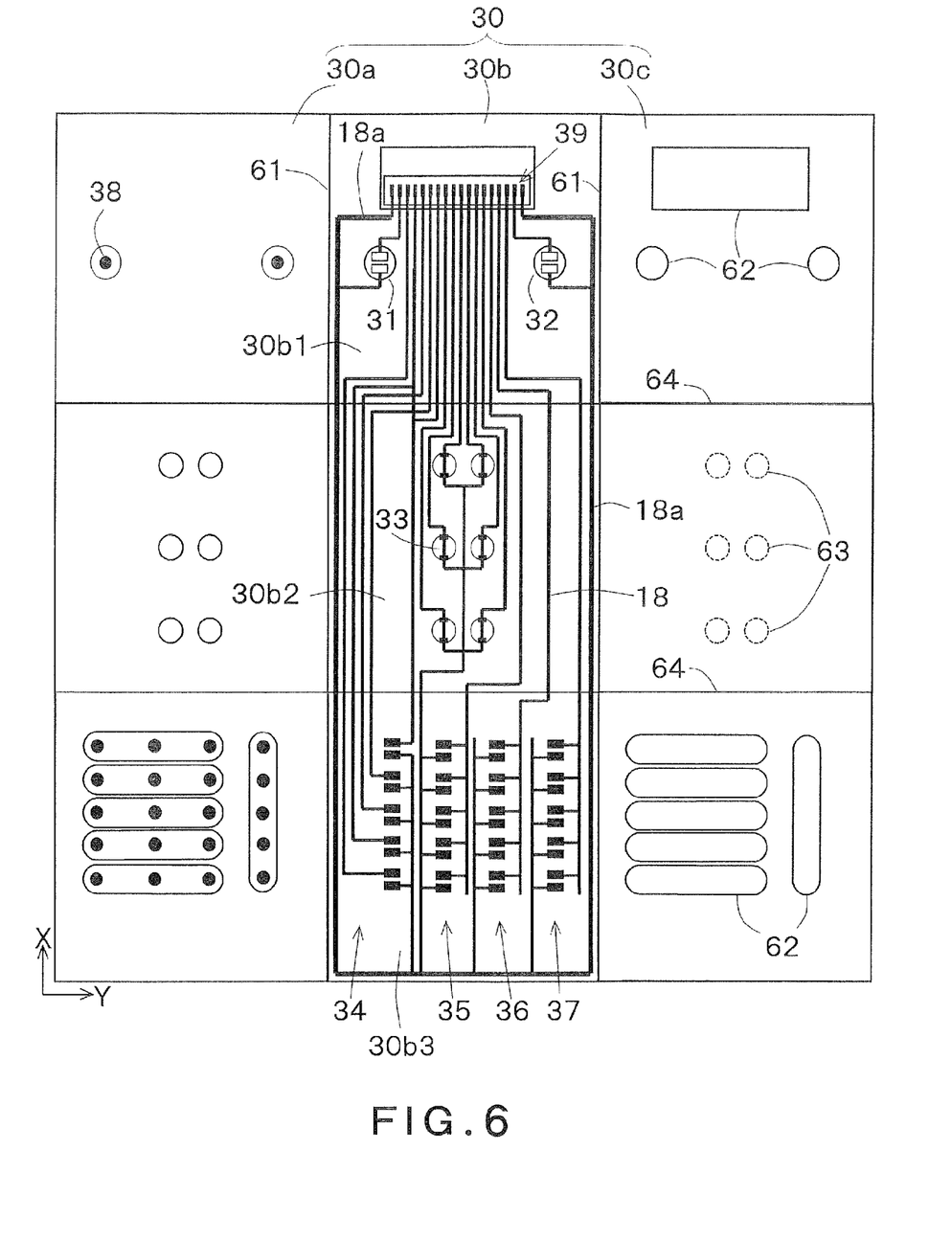
FIG. 6 A development view of a paper substrate 30 serving as the base of the dose record card 1.

FIG. 6 is a development view of a paper substrate 30 serving as the base of the dose record card 1. Divisional substrates 30a, 30b, and 30c are obtained by dividing the paper substrate 30 of FIG. 6 into three in the longitudinal direction along folding lines 61, the divisional substrates having different conductive patterns 18, openings, etc. Note that these three divisional substrates 30a-30c are foldable along the folding lines 61, and are not physically separated from each other.

The divisional substrate 30b in the middle of FIG. 6 is a lowermost substrate 30b arranged in the bottom layer and having the conductive patterns 18 formed thereon. The divisional substrate 30c on the right side of the lowermost substrate 30b is an intermediate substrate 30c arranged on the lowermost substrate 30b and having mainly openings 62 and perforations 63. The divisional substrate 30a on the left side of the lowermost substrate 30b is an uppermost substrate 30a arranged on the intermediate substrate 30c and having conductive patterns 38 for establishing/breaking electrical continuity of switch contacts.

As mentioned later, the structure of FIG. 2 can be obtained by dividing the paper substrate 30 into three, folding the intermediate substrate 30c over the lowermost substrate 30b, bonding them through thermo-compression, folding the uppermost substrate 30a over the intermediate substrate 30c, and bonding them through thermo-compression. Therefore, the back face of the uppermost substrate 30a shown in FIG. 6 corresponds to the information input face 2 shown in FIG. 2.

Before folding the intermediate substrate 30c over the lowermost substrate 30b to bond them through thermo-compression, the communication module 10 is joined on the lowermost substrate 30b and the intermediate substrate 30c is bonded thereon through thermo-compression. In this way, the communication module 10 is sandwiched between the lowermost substrate 30b and the intermediate substrate 30c. Accordingly, the conductive patterns 18 and the communication module 10 formed on the lowermost substrate 30b are not visible externally when the dose record card 1 is completed. Similarly, the conductive patterns on the uppermost substrate 30a are not visible externally since the uppermost substrate 30a is folded over the intermediate substrate 30c and these are bonded through thermo-compression.

Next, the conductive patterns 18 formed on the lowermost substrate 30b will be explained using FIG. 6. The conductive patterns 18 of FIG. 6 are formed on first to third pattern faces 30b1 to 30b3 corresponding to the first to third faces 2a to 2c obtained by dividing the information input face 2 into three in the lateral direction.

The first pattern face 30b1 has a switch contact 31 corresponding to the start button 3, and a switch contact 32 corresponding to the cancel button 4. The second pattern face 30b2 has six switch contacts 33 corresponding to the cases of the pills 5. The third pattern face 30b3 has 15 switch contacts 34 to corresponding to the selection buttons for selecting the symptom and symptom level of the patient.

Of the switch contacts 31 to 37, the six switch contacts 33 corresponding to the cases of the pills 5 are electrically connected in the initial state, and the other switch contacts 31, 32, and 34 to 37 are electrically disconnected in the initial state.

The switch contact 33 corresponding to the case of each pill 5 is physically broken and electrically disconnected when the case is pressed to take out the pill. Each of the other switch contacts 31, 32, and 34 to 37 is electrically connected temporarily only while its corresponding button is pressed and the circular conductive pattern 38 provided on the back face of the information input face 2 touches its corresponding switch contact.

As stated above, in the initial state, some of the switch contacts 31 to 37 are electrically connected while the others are electrically disconnected. The state of each switch contact can be switched by physically breaking the switch contact, or by bringing the switch contact into contact with another conductive pattern.

One ends of the switch contacts 31 to 37 shown in FIG. 6 are connected to their corresponding terminals in a terminal unit 39 on the first pattern face 30b1 through the conductive patterns 18, and the other ends thereof are connected to a ground terminal through the conductive patterns 18. The terminal unit 39 has terminals corresponding to the total number of switch contacts, and ground terminals provided on the both sides of the terminal unit 39. The conductive pattern (hereinafter referred to as ground pattern 18a) extending from the ground terminals is formed along the outer edge of the first to third pattern faces 30b3 to surround other conductive patterns and switch contacts. This ground pattern 18a is formed thicker than the other conductive patterns to reduce noises.

As stated above, every switch contacts is connected between its corresponding terminal and the ground pattern 18a. Therefore, when the state of any one switch contact changes, information about the change is transmitted to the communication module 10 through a dedicated terminal. The storage 21 in the communication module 10 stores information for identifying the switch contact whose state changed and information about the time when the state of the contact point changed.

The switch contacts on the third pattern face 30b3 are grouped into a first switch contact line 34 corresponding to the first button line arranged in the X-direction, and second switch contact lines 35 to 37 corresponding to the second button lines arranged in the Y-direction to be nearly in parallel to the first button line.

One ends of five switch contacts constituting each of the second switch contact lines 35 to 37 are connected to a common terminal, and the other ends thereof are connected to the ground terminal. These five switch contacts are connected in parallel. The example of FIG. 6 shows three second switch contact lines 35 to 37 each having five switch contacts connected in parallel.

When there is a change in the state of any one of switch contacts 35 to 37 connected in parallel, information about the state change is transmitted to the communication module 10 through the same terminal, which means that the information is not enough to enable the communication module 10 to identify which switch contact changed. Thus, in the present embodiment, the state of a switch contact in the first switch contact line 34 should be changed before changing the state of a switch contact in the second switch contact lines 35 to 37, which is a rule defined to identify which one of the switch contacts in the second switch contact lines 35 to 37 changed.

More concretely, the state of any one switch contact in the first switch contact line 34 is changed first, to detect the position of this switch contact in the X-direction. Then, three switch contacts which are included in the second switch contact lines 35 to 37 and positioned in the same X-direction are determined as selection options. Next, if the state of any one of these three switch contacts changed, information about the switch contact is transmitted to the communication module 10.

As stated above, the combination of information about a change in the state of a switch contact in the first switch contact line 34 and information about a change in the state of a switch contact in the second switch contact lines 35 to 37 makes it possible to correctly transmit the state of a specific switch contact in the second switch contact lines 35 to 37 to the communication module 10.

Connecting one ends of a plurality of parallel-connected switch contacts to a common terminal achieves reduction in the total number of terminals in the terminal unit 39 and the number of the conductive patterns 18, which is effective particularly when the pattern area is limited. Although a plurality of switch contacts in the second switch contact lines 35 to 37 are connected in parallel, there is no practical problem, since the state of a specific switch contact in the second switch contact lines 35 to 37 can be correctly identified by referring to the state of a switch contact in the first switch contact line 34 arranged in parallel to the second switch contact lines 35 to 37.

Figure 7:
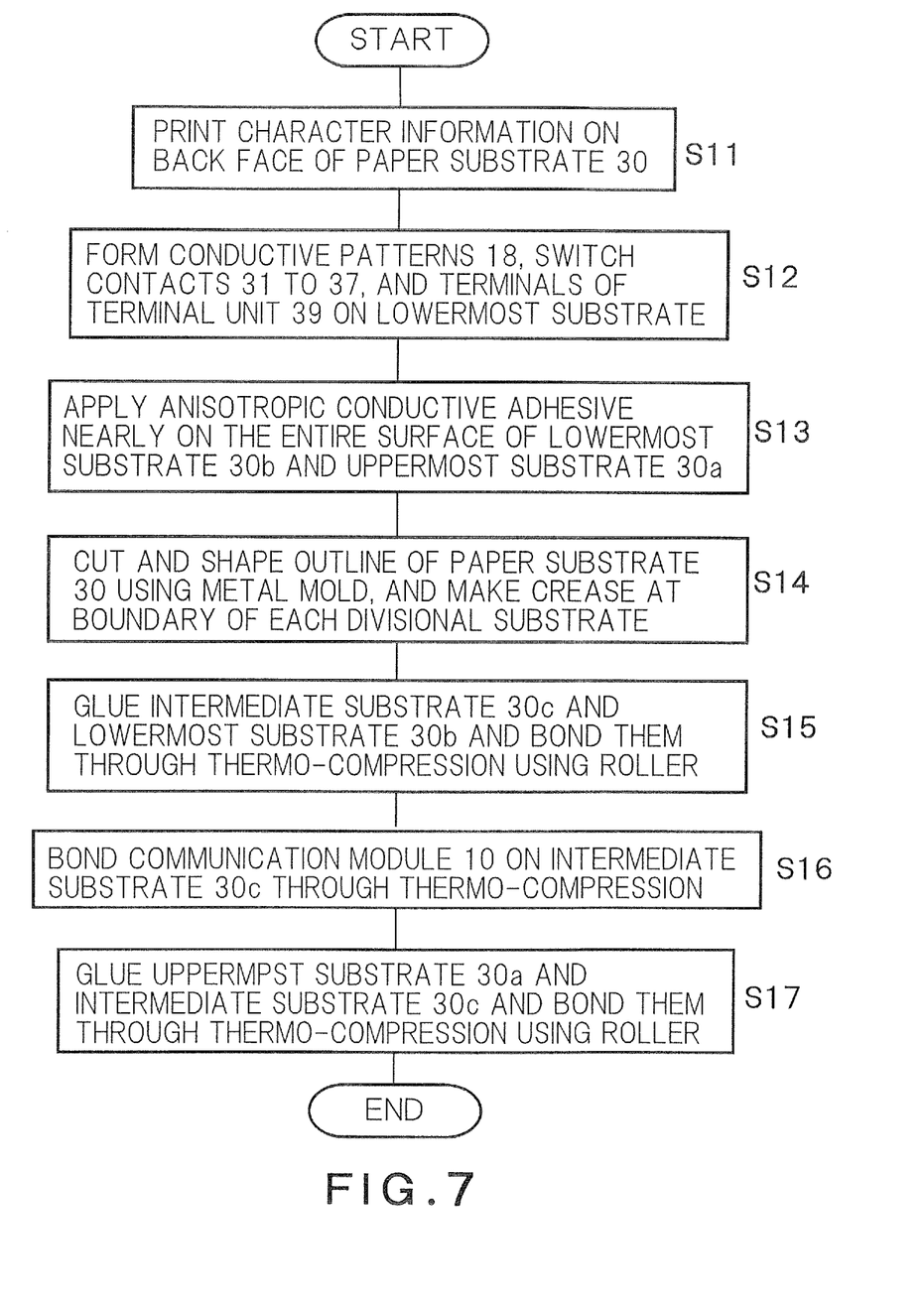
FIG. 7 A diagram explaining a manufacturing process of the dose record card 1 according to the first embodiment.

FIG. 7 is a diagram explaining a manufacturing process of the dose record card 1 according to the first embodiment. Hereinafter, a manufacturing process of the dose record card 1 according to the first embodiment will be explained using FIG. 7. First, predetermined character information (e.g., character information on the face of FIG. 1 or FIG. 2) is printed on the back face of the paper substrate 30 having the size as shown in FIG. 6 (Step S11). Next, the conductive patterns 18, switch contacts 31 to 37, and terminals of the terminal unit 39 are formed on the lowermost substrate 30b in the middle of the three divisional substrates shown in FIG. 6 (Step S12). Similarly, the circular conductive patterns 38 are formed on the uppermost substrate 30a, corresponding to the positions of the switch contacts. These are formed through serigraph using, e.g., conductive carbon, copper oxide, or silver.

Next, anisotropic conductive adhesive is applied nearly on the entire surface of the lowermost substrate 30b and uppermost substrate 30a, avoiding the parts around the switch contacts 31 to 37, the location of the communication module 10, and the parts around the conductive patterns 38 (Step S13). Even when this anisotropic conductive adhesive, which has electroconductivity only in one direction (X-direction), is applied on the terminals of the terminal unit 39 and on the conductive patterns 18, there is no fear that different terminals are short-circuited to each other.

Note that it is also possible to attach a conductive adhesive tape only to the terminal unit 39, while applying non-conductive adhesive on the other parts. The basic material of the adhesive or adhesive tape is epoxy resin or acrylic resin compounded with particles of a conductive material.

Next, the outline of the paper substrate 30 is cut and shaped using a metal mold, and the folding line 61 is formed at the boundary of each divisional substrate by performing a creasing process (Step S14). In this process, on the intermediate substrate 30c, the holes (openings) 62 are formed at the positions corresponding to the communication module 10 and respective buttons, and the perforations 63 are formed at the positions corresponding to the pills 5. Further, folding lines 64 are formed in each divisional substrate to divide the divisional substrate into three in the lateral direction.

Next, the intermediate substrate 30c is folded over the lowermost substrate 30b along the folding line 61 to glue and bond the divisional substrates through thermo-compression using a roller (Step S15).

Next, the communication module 10 is mounted on the first pattern face 30b1 exposed through a hole provided in the intermediate substrate 30c (Step S16). Here, the pads 16 of the communication module 10 are positionally adjusted to the terminal unit 39 on the first pattern face 30b1, and those are bonded through thermo-compression using the above-mentioned anisotropic conductive adhesive or conductive tape.

Next, the uppermost substrate 30a is folded over the intermediate substrate 30c along the folding line 61 to glue and bond the divisional substrates through thermo-compression using a roller (Step S17). By performing the process as stated above, the dose record card 1 shown in FIG. 2 is completed.

As stated above, the dose record card 1 according to the first embodiment has the cancel button 4 for cancelling the button operation immediately before the cancel button 4 is pressed, in addition to various selection buttons such as the start button 3, which eliminates the fear that incorrect information due to incorrect button operation is transmitted to the communication module 10 without cancel information, and improves reliability of the information transmitted to the communication module 10 and host computer.

Further, the cancel button 4 can reduce a mental burden on the patient thinking that no mistake is acceptable in the button operation.

Further, since parallel-connected switch contacts corresponding at least a part of selection buttons 35 to 37 are connected to the same terminal, selection buttons can be provided in the card as many as possible without being influenced by the total number of terminals in the terminal unit 39 and the number of the pads 16 of the communication module 10. This makes it possible to store various types of selection information in the communication module 10, and to gather the efficacy of medicine taken by the patient in more detail. Further, although a plurality of parallel-connected switch contacts are connected to the same terminal, there is no practical problem, since information about the press of a specific button can be correctly detected and transmitted to the communication module 10 by referring to other switch contacts.

Further, since the switch contacts corresponding to the selection buttons 35 to 37 are connected in parallel, the arrangement of the selection buttons 35 to 37 can be arbitrarily changed, which increases degrees of freedom of the arrangement of the buttons while making it easy to select a user-friendly button arrangement for lessening the frequency of incorrect operation.

Second Embodiment

A second embodiment to be explained below is characterized in the arrangement of switch contacts which is different from the first embodiment.

Figure 8:
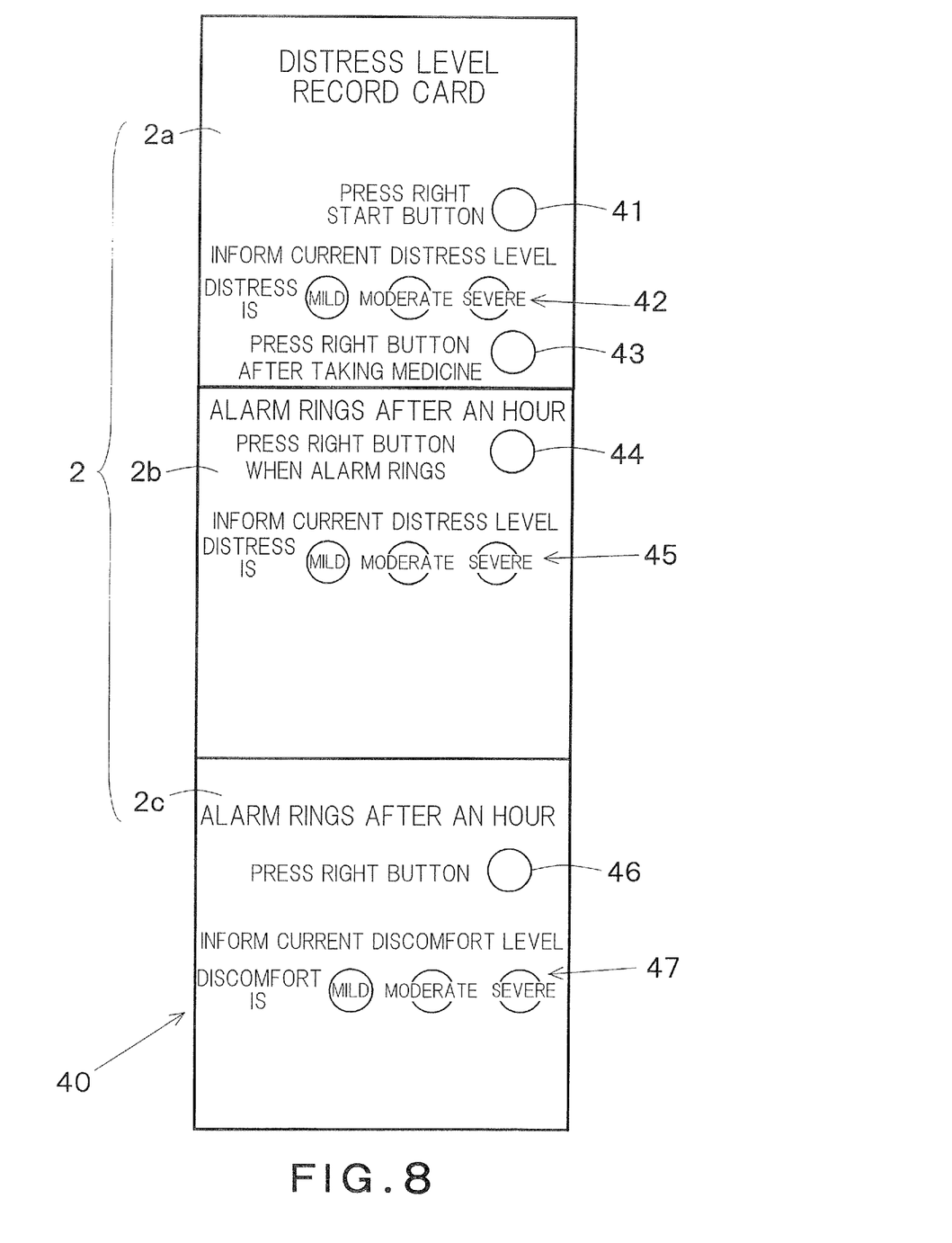
FIG. 8 A diagram showing the information-gathering device according to a second embodiment of the present invention.
Figure 9:
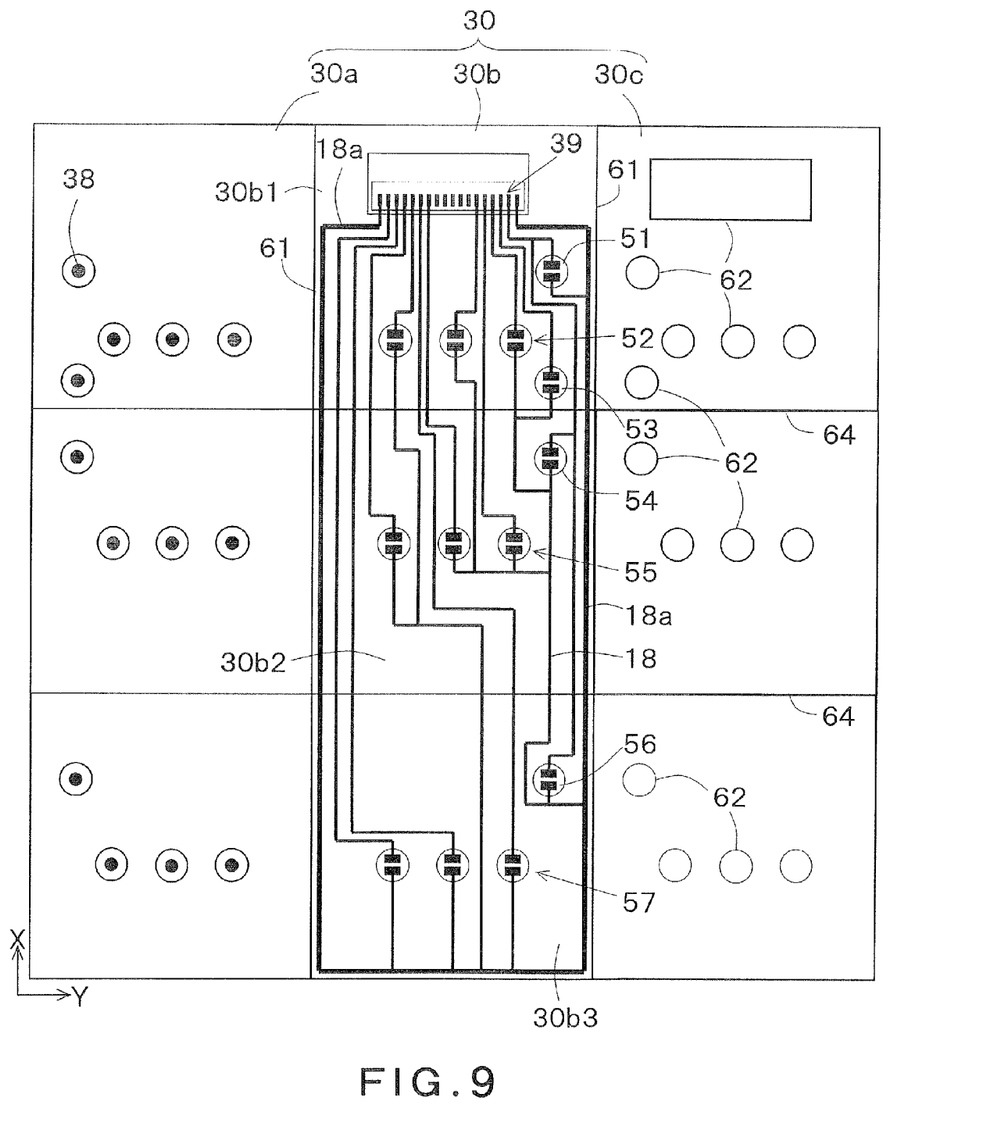
FIG. 9 A development view of the information-gathering device of FIG. 8.

FIG. 8 is a diagram showing the information-gathering device according to the second embodiment of the present invention. The information-gathering device of FIG. 8 is a distress level record card 40 for recording the distress level of the patient, and FIG. 9 shows a development view thereof. Folding this development view leads to an appearance similar to FIG. 1.

The distress level record card 40 of FIG. 8 has the information input face 2 having the first to third faces 2a to 2c. The first face 2a has a start button (start instruction button) 41, three selection buttons 42 for selecting a distress level of the patient, and a dose record button 43 to be pressed after taking medicine. The second face 2b has a stop button 44 (start instruction button) 44 for stopping alarm, and three selection buttons 45 for selecting a distress level of the patient. The third face 2c has a start button 46 for starting checking a discomfort level, and three selection buttons 47 for selecting a discomfort level of the patient.

In the distress level record card 40 of FIG. 8, when the patient presses the dose record button 43 after taking medicine, the alarm automatically rings one hour later. When the alarm rings, the patient first stops the alarm by pressing the stop button 44, and then selects a distress level again.

After pressing the start button on the first face 2a, the patient operates buttons sequentially from the top to the bottom following instructions, which is the use originally intended. As a general rule, it is required to correctly press a specified button in the button operation. However, it may be difficult for the patient confused with a sudden alarm ring to find the stop button 44 immediately. As a result, the alarm continues ringing for a long time, which may impose an unnecessary mental burden on the patient.

Accordingly, in the present embodiment, the same function can be fulfilled by pressing any one of the start buttons 41 and 46 and stop button 44. That is, when any one of the start buttons 41 and 46 and stop button 44 is pressed, the same selection information is transmitted to the communication module 10. Thus, the patient is allowed to press any one of the three buttons, i.e. the start buttons 41 and 46 and stop button 44, to stop the alarm. This makes it possible to select a button easily, which leads to the improvement of the convenience of the patient.

Further, in the distress level record card 40 of FIG. 8, after pressing any one of the start buttons 41 and 46 or after pressing the stop button 44, the patient is required to select a distress level or a discomfort level from the selection buttons 42, 45, and 47. Since these selection buttons are provided corresponding to each of the start buttons 41 and 46 and stop button 44, it is possible to correctly detect whether the selection button pressed by the patient shows the distress level initially selected, the distress level selected again after that, or the discomfort level selected after that. Thus, press information about the selection buttons 42, 45, and 47 can be correctly transmitted to the communication module 10, regardless of which one of the two start buttons 41 and 46 and stop button 44 was pressed by the patient.

Accordingly, in the present embodiment, the patient is allowed to press any one of the two start buttons 41 and 46 and stop button 44 before pressing the selection buttons 42, 45, and 47 concerning distress level or discomfort level.

For example, when the alarm starts ringing, the patient may stop the alarm by pressing the start button 41 or 46 on the first information input face 2 or third information input face 2, before selecting a selection button on the second information input face 2.

FIG. 9 shows three divisional substrates obtained by dividing the distress level record card 40 of FIG. 8 into three in the longitudinal direction. The lowermost substrate 30b in the middle has the first to third pattern faces 30b1 to 30b3 obtained by dividing the lowermost substrate 30b into three in the lateral direction. Each pattern face has switch contacts 51 to 57 corresponding to the start buttons 41 and 46, stop button 44, and selection buttons. Further, the uppermost substrate 30a on the left side of the lowermost substrate 30b has the circular conductive patterns 38 for switching between electrical connection and disconnection of the switch contacts.

As stated above, in the present embodiment, the same function can be fulfilled by pressing any one of the two start buttons 41 and 46 and stop button 44, without identifying each button. In order to achieve this feature, the three switch contacts 51, 54, and 56 corresponding to the three buttons 41, 44, and 46 are connected in parallel so that one ends of the switch contacts are connected to a common terminal and the other ends thereof are connected to a ground terminal. Thus, when any one of the two start buttons 41 and 46 and stop button 44 is pressed, the same press information is transmitted to the communication module 10.

As stated above, in the second embodiment, so that the same function is fulfilled when any one of the switch buttons 41 and 46 and stop button 44 is pressed, switch contacts 51, 54, and 56 corresponding to these buttons are connected in parallel, one ends thereof are connected to a common terminal and the other ends thereof are connected to a ground terminal. Accordingly, the patient can press a button at the position he/she can press easily, which improves convenience. Particularly, when quick response is required for the patient to stop the sound of the alarm for example, the patient has no need to make an effort to search a button, which prevents a mental burden on the patient.

Another Modification Example

Each of the first and second embodiments is shown as an example, and any changes may be made in the arrangement and number of various buttons, the arrangement and number of switch contacts corresponding to the buttons, forms of the conductive patterns 18 connected to the switch contacts, and the number of terminals of the terminal unit 39, depending on the intended use of the information-gathering device.

The characteristics of the first embodiment and the characteristics of the second embodiment may be arbitrarily combined together. For example, the distress level record card 40 according to the second embodiment may have a cancel button, or the dose record card 1 according to the first embodiment may have a plurality of buttons having the same function.

The information-gathering devices according to the first and second embodiments should not be limited only to the dose record card 1 and distress level record card 40, and can be applied to various purposes (e.g., follow-up record card for diabetes treatment, follow-up record card for rheumatism treatment, pain/dose record card, etc.) Further, the information-gathering device should not be necessarily limited to medical purposes, and may be used for various purposes such as questionnaire gathering, as long as the information-gathering device can record any information and transmit the recorded information to the host computer through wireless communication.

The assembly structure of the information-gathering devices according to the first and second embodiments should not be limited to FIG. 6 etc. The base material should not be necessarily paper, and may be replaced with another material such as resin. Further, the communication module 10 should not be necessarily a cell-driven type, and may be driven without a battery by accumulating power received through NFC to perform wireless communication using the accumulated power.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A sheet-like information-gathering device comprising:
a plurality of selection buttons to be pressed by a user; and
a communication module capable of storing at least identification information about the user and information about a pressed selection button, to wirelessly transmit the stored information to a host device, comprising:
a cancel button to cancel the information about the selection button pressed by the user,
wherein the communication module has an IC chip and a button cell which supplies power-supply voltage to this IC chip,
the IC chip comprising:
a storage configured to store information which identifies the pressed selection button and information about the time of the press, in chronological order;
a controller configured to perform control to store the information in the storage; and
a wireless communication unit configured to perform close proximity wireless communication with the host device,
the controller, when the cancel button is pressed, to store, in the storage, information requesting to cancel press information about the selection button pressed immediately before the cancel button is pressed.

2. The information-gathering device of claim 1,
wherein at least a part of the selection buttons are arranged in two-dimensional directions so that a plurality of selection buttons are arranged in each direction,
the selection buttons arranged in the two-dimensional directions comprising:
a first button line having a plurality of selection buttons arranged in a first direction; and
a plurality of second button lines arranged in a second direction to be nearly in parallel to the first button line, and
the controller stores, in the storage, a combination of press information about one selection button selected from the first button line and press information about a plurality of selection buttons which are included in the second button lines and located on a line identical to the line of the selected selection button.

3. The information-gathering device of claim 2, comprising:
a plurality of switch contacts formed on a sheet substrate, corresponding to the selection buttons;
a terminal unit having a plurality of terminals arranged on a line on the sheet substrate; and
a plurality of conductive patterns connecting the switch contacts to the terminals,
wherein the switch contacts comprise:

a first switch contact line provided corresponding to the first button line, the first switch contact line having a plurality of switch contacts arranged in the first direction; and
second switch contact lines provided corresponding to the second button lines, each second switch contact line having a plurality of switch contacts arranged in the second direction to be nearly in parallel to the first button line, and
one ends of the switch contacts arranged in the first direction in the second switch contact lines are connected to an identical terminal in the terminal unit, and the other ends thereof are connected to a ground terminal of the terminal unit.

4. The information-gathering device of claim 1, wherein the controller can store new information in the storage within storage capacity of the storage, but the controller is inhibited to eliminate and overwrite the information already stored in the storage.

5. The information-gathering device of claim 1, wherein the controller stores, in the storage, information which identifies a pressed button selected from the selection buttons and the cancel button together with information about the time when the button was pressed.

6. The information-gathering device of claim 1, further comprising a sheet member made of paper or plastic and capable of being folded to form a plurality of layers, each layer having the selection buttons on its surface, and the communication module is sandwiched between two layers adjacent to each other.

7. An information-gathering device comprising:
a plurality of buttons arranged on a first layer of a sheet substrate, to be arbitrarily selected;
a plurality of switch contacts arranged on a second layer of the sheet substrate, corresponding to the buttons;
a terminal unit having a plurality of terminals arranged on a line on the second layer; and
a plurality of conductive patterns arranged on the second layer, to connect the switch contacts to the terminals,
wherein two or more of the buttons are partially arranged in one direction so that one ends of switch contacts corresponding to the buttons are connected to an identical terminal of the terminal unit through the conductive patterns, and that the other ends thereof are connected to a ground terminal of the terminal unit through the conductive patterns.

8. The information-gathering device of claim 7,
wherein the buttons comprise:
a plurality of button lines each having two or more buttons showing two or more options, one of which is to be selected; and
a plurality of start instruction buttons instructing to start selection from each button line,
wherein one ends of a plurality of switch contacts corresponding to the start instruction buttons are connected to an identical terminal of the terminal unit through the conductive patterns, and the other ends thereof are connected to a ground terminal of the terminal unit through the conductive patterns.

9. The information-gathering device of claim 8, wherein at least one of the start instruction buttons also instructs to stop an alarm ring.

10. The information-gathering device of claim 7, wherein the sheet substrate is a sheet member made of paper or plastic and capable of being folded to form a plurality of layers, each layer having the selection buttons on its surface, and the switch contacts and the conductive patterns are sandwiched between two layers adjacent to each other.

* * * * *